(12) United States Patent
Loch et al.

(10) Patent No.: US 6,509,558 B1
(45) Date of Patent: Jan. 21, 2003

(54) OPTICAL SENSOR FOR MEASURING OPAQUENESS OF WASHING OR RINSING LIQUID

(75) Inventors: Christian Loch, St. Wendel (DE); Clemens Jung, Bexbach (DE); Gerhard Kersten, Schmelz (DE)

(73) Assignee: Whirlpool Corporation, Benton Harbor, MI (US)

( * ) Notice: Subject to any disclaimer, the term of this patent is extended or adjusted under 35 U.S.C. 154(b) by 0 days.

(21) Appl. No.: 09/353,246

(22) Filed: Jul. 14, 1999

(30) Foreign Application Priority Data

Jul. 15, 1998 (DE) .......................... 198 31 688

(51) Int. Cl.⁷ .................. H01J 40/14; G01N 21/49; D06E 37/00; B08B 3/00
(52) U.S. Cl. .................. 250/222.2; 356/436; 356/440; 134/113; 68/12.02; 250/573
(58) Field of Search ............... 250/222.2, 573; 356/72, 436, 440, 442, 339; 68/12.02, 12.27; 134/113

(56) References Cited

U.S. PATENT DOCUMENTS

| | | | | |
|---|---|---|---|---|
| 3,510,666 A | * | 5/1970 | Topol | .......................... 250/574 |
| 4,257,708 A | * | 3/1981 | Fukuda | .......................... 250/565 |
| 5,140,168 A | | 8/1992 | King | |
| 5,241,845 A | * | 9/1993 | Ishibashi et al. | ........... 68/12.02 |
| 5,291,626 A | | 3/1994 | Molnar et al. | |
| 5,446,531 A | | 8/1995 | Boyer et al. | |

FOREIGN PATENT DOCUMENTS

| | | | |
|---|---|---|---|
| DE | 42 42 927 A | 6/1994 | .......... G01N/21/55 |
| DE | 196 26 203 A | 1/1998 | .......... G01N/21/47 |
| EP | 653 620 A | 10/1994 | .......... G01N/21/03 |
| FR | 178031 | * 10/1985 | |

OTHER PUBLICATIONS

European Search report #99113041 dated Oct. 29, 1999.

* cited by examiner

*Primary Examiner*—Zandra Smith
(74) *Attorney, Agent, or Firm*—Robert O. Rice; Stephen D. Krefman; Thomas J. Roth

(57) ABSTRACT

The invention concerns an optical sensor for measuring the property of a gaseous or liquid medium, particularly the opaqueness of a washing or rinsing liquid in a washing or rinsing machine, with at least one radiation source, a radiation receiver and a light-transmitting sensor body, with an optical boundary surface, which, depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index conditions at the boundary surface. Unambiguous measurement signals for process control of a washing or rinsing machine are obtained through separate sensing of the transparency and reflection of the medium.

12 Claims, 3 Drawing Sheets

OPTICAL SENSOR FOR MEASURING OPAQUENESS OF WASHING OR RINSING LIQUID

BACKGROUND OF THE INVENTION

1. Field of the Invention

The invention concerns an optical sensor for measuring the property of a gaseous or liquid medium, particularly the opaqueness of a washing or rinsing liquid in a washing or rinsing machine, with at least one radiation source, a radiation receiver and a light-transmitting sensor body, with an optical boundary surface, which, depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index relationships at the boundary surface.

2. Description of the Related Art

An optical sensor of this type is known from the DE 42 42 927 A1. This known sensor has a single radiation source and a single radiation receiver and the different measurement signals are based on a combination of the physical effects of reflection and variation of the refractive index relationship at the boundary surface of the lens-type sensor body. The measurement signals permit differentiation in foam, air and liquid outside the sensor body. In this case only differentiation is effected by the measurement signal in the presence of water, air or foam. This optical sensor is not adequate for the purpose of determining unambiguously the opaqueness of the washing or rinsing liquid in a washing or rinsing machine since if the liquid is dirty to a greater or lesser degree the measurement signal obtained is essentially the same. Since differing dirtiness of the water is the single-valued criterion of the progress of the process cycle in a washing or rinsing machine and thus of sensor-controlled changing of the program, an optimum process control cannot be established with the known sensor.

SUMMARY OF THE INVENTION

It is therefore the object of the invention to create an optical sensor, of the type initially referred to, by means of which it is possible to derive unambiguously differentiable measurement signals for the degree of opaqueness of a liquid medium in a washing or rinsing machine which can be used for process control.

This object is achieved, according to the invention, in that an additional radiation source for detecting the transparency of the medium directs a radiation through the medium and the sensor body on to the radiation receiver and in that the radiation receiver emits in chronological succession the measurement signals which are initiated by the two time-multiplexed radiation sources and which characterise the transparency and reflection of the medium, or in that an additional radiation source for detecting the transparency of the medium directs a radiation through the medium on to an additional receiver and in that the two radiation receivers simultaneously emit the measurement signals which are initiated by the assigned radiation sources and which characterise the transparency and reflection of the medium.

The sensing of the transparency of the medium also measures its degree of opaqueness, so that different measurement signals, which can be used for process control, are obtained according to the degree of dirtiness. In the first case, the time multiplex operation means that only an additional radiation source is required, whereas in the second case parallel determinations are obtained concerning the reflectivity and transparency of the medium with the use of an additional radiation receiver. By contrast with the known optical sensor, therefore, in the case of water being present as a medium simultaneous differentiation is still possible in different degrees of dirtiness of the medium, this being of considerable advantage for control of the process, i.e., changing of the programs, for the purpose of optimising the process according to time, temperature, water and energy and adapting it to different conditions.

For the purpose of obtaining unambiguous measurement signals in measurement of the transparency, there is provision, according to one embodiment, whereby the radiation source for measuring the transparency of the medium directs the radiation through the medium, transversely relative to the direction of flow of the latter.

If the arrangement is such that the boundary surface of the lens-type sensor body faces towards the medium and forms a part of a light-transmitting sensor casing which itself forms a part of the channel through which the medium flows, and such that at least the boundary surface of the sensor body projects into the channel, then differentiation also occurs in the presence of air or foam.

The construction of the optical sensor is such that the sensor casing accommodates the radiation sources and the radiation receivers, the radiation source provided to detect the reflection of the medium and the single radiation receiver being disposed on the sensor body, facing away from the boundary surface of the sensor body, whereas the radiation source provided to detect the transparency of the medium and any additional radiation receiver provided for the latter are disposed outside the sensor body, in the sensor casing or in the channel.

If only a single radiation receiver is provided for detecting the transparency and the reflection of the medium, then, for the purpose of detecting the transparency, the optical sensor can be designed so that the sensor casing comprises in addition to the sensor body a chamber, projecting into the channel and the medium, in which is inserted the radiation source provided for detecting the transparency of the medium, which directs its radiation through the medium on to the boundary surface of the sensor body, or so that the sensor casing forms in addition to the sensor body a light guide, projecting into the medium and the channel, which deflects the radiation emitting from the radiation source for detecting the transparency of the medium and directs it through the medium on to the boundary surface of the sensor body.

The arrangement can also be designed so that the radiation source provided for detecting the transparency of the medium is disposed on the side of the channel opposite to the sensor body and so that the radiation emitting from this radiation source is directed through the sensor body on to the single radiation receiver.

The radiation sources are formed, most simply, by light-emitting diodes and the radiation receivers by phototransistors.

BRIEF DESCRIPTION OF THE DRAWINGS

The invention is described more fully with reference to three embodiment examples, depicted in the drawings, wherein.

DESCRIPTION OF THE PREFERRED EMBODIMENT

Figure 1:
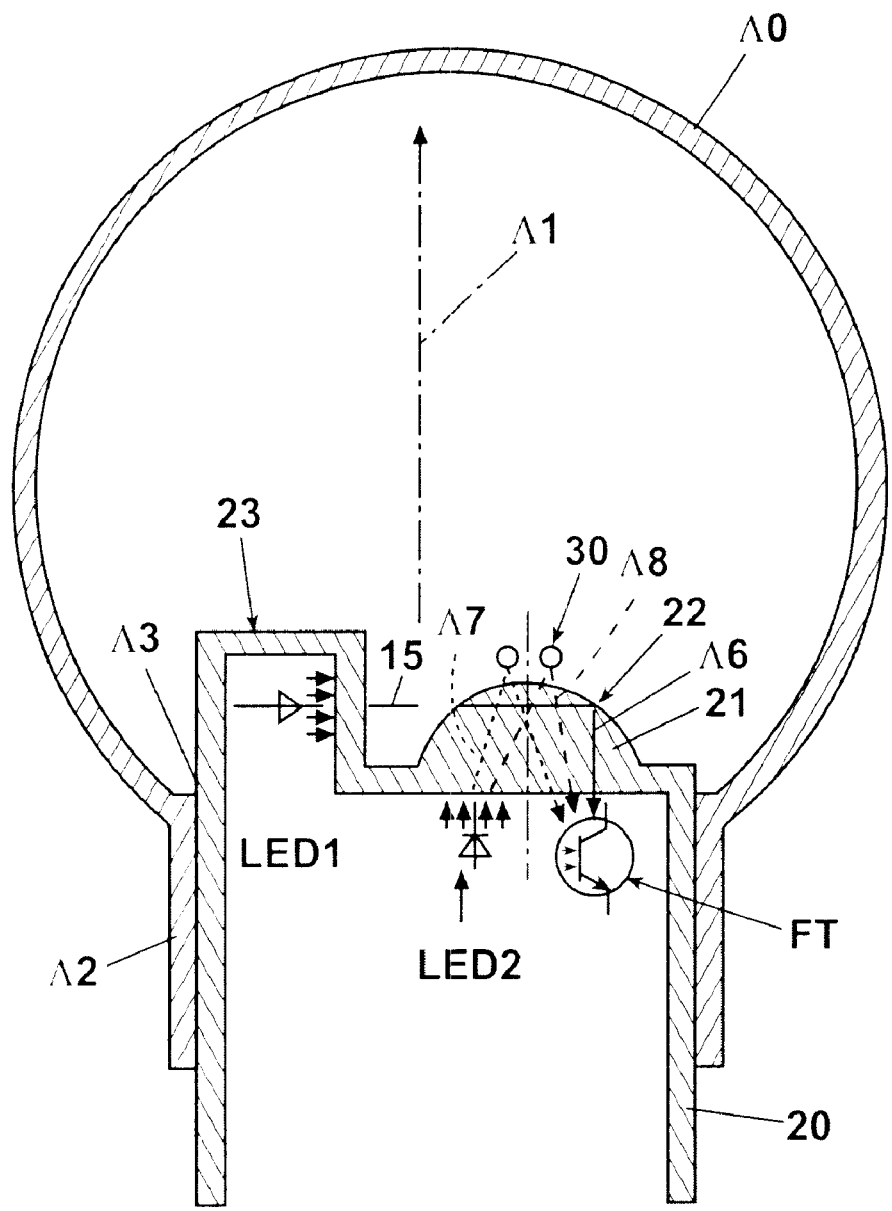
FIG. 1 shows a sectional drawing of an optical sensor, in a line carrying the medium.

The channel 10 carrying the medium 11, e.g. the washing or rinsing liquid, is a hose line of a washing or rinsing machine, in which the washing or rinsing liquid can circulate. With the flanges 12, the channel 10 forms a receptacle 13 for a sensor casing 20 made from light-transmitting material. A part of the sensor casing 20 is fashioned as a lens-type sensor body 21, with the boundary surface 22, which projects into the channel 10. Disposed on the straight surface of the sensor body 21, opposite the boundary surface 22, are a radiation source LED2 in the form of a light-emitting diode and a radiation receiver FT in the form of a phototransistor. When the radiation source LED2 is operated, it generates a wide light beam 17 which is returned to a greater or lesser extent to the radiation receiver FT, as shown by the radiation 18, depending on the refractive index at the boundary surface 22 and/or the reflection on foam bubbles 30. In this case, the optical sensor operates like the sensor known from DE 42 42 927 A1 and provides differentiable measurement signals for water, air or foam.

The arrow denoted by reference 11 in FIG. 1 shows the direction of flow of the medium 11. The sensor casing 20 forms, in addition to the sensor body 21, a chamber 23 which also projects into the channel 10 and accommodates an additional radiation source LED1 for detecting the transparency of the medium 11. The light-emitting diode is set so that its radiation 15 passes transversely relative to the medium 11 and meets the boundary surface 22. The radiation 15 is weakened to a greater or lesser extent by the degree of opaqueness, i.e. the dirtiness of the medium 11, so that only a portion 16 is reflected at the boundary surface 22 and delivered to the radiation receiver FT. The reflected portion 16 of the radiation 15 decreases as the degree of dirtiness of the medium 11 increases, so that in this case the radiation receiver FT emits a measurement signal which is dependent on the degree of opaqueness. In order that the transparency and reflection of the medium can be measured independently of one another, the radiation sources LED1 and LED2 are time-multiplexed, resulting in a chronologically successive emission of corresponding measurement signals at the single radiation receiver FT. It is also obvious that an additional radiation receiver (not depicted) can also be provided, taking account of the direction of radiation of the additional radiation source LED1 for detecting the transparency, for the purpose of obtaining parallel and simultaneous measurement signals for the transparency and reflection of the medium 11.

Figure 2:
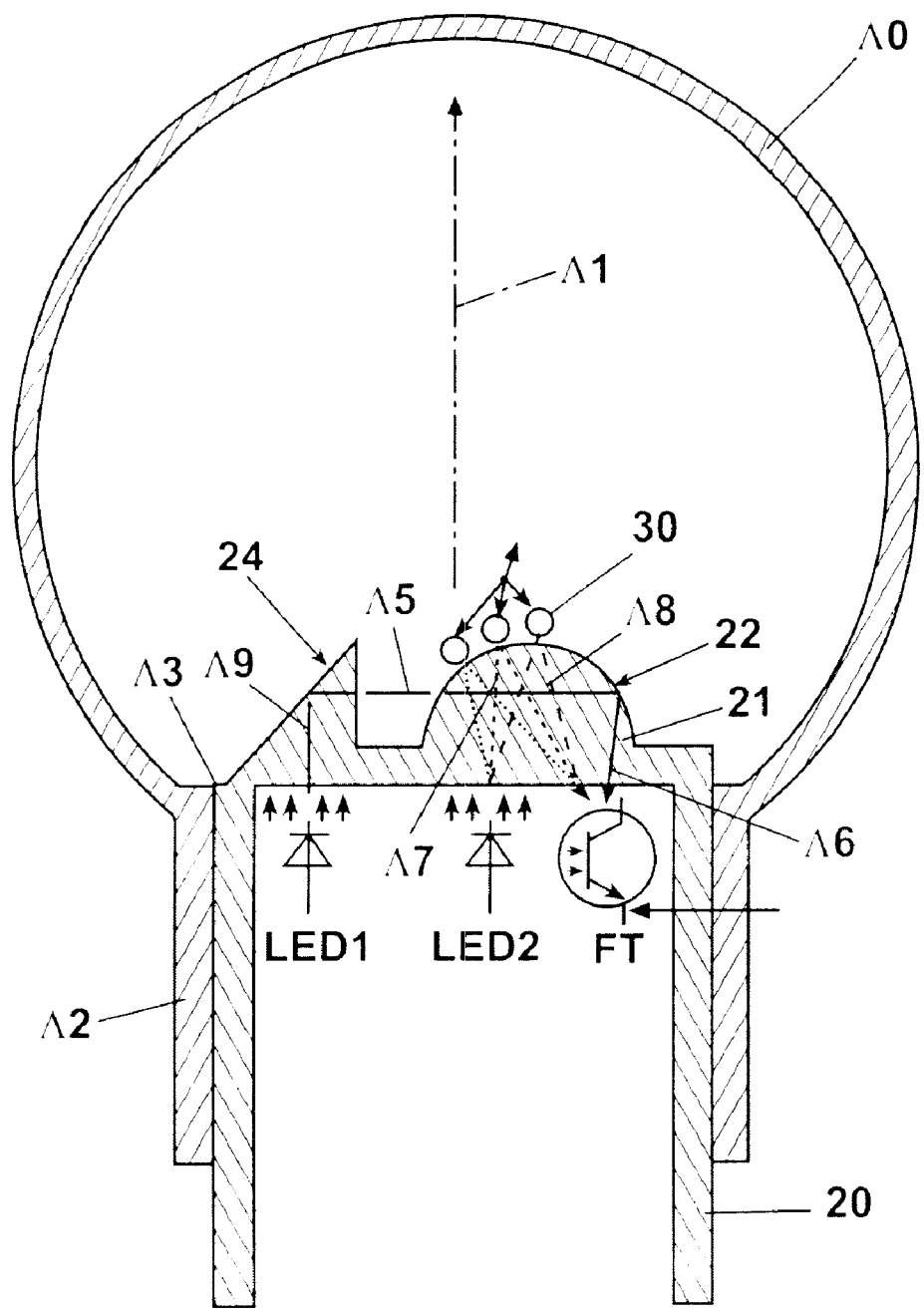
FIG. 2 shows a sectional drawing of an optical sensor, equivalent to FIG. 1, with a different guidance of the radiation generated for detecting the transparency.
Figure 3:
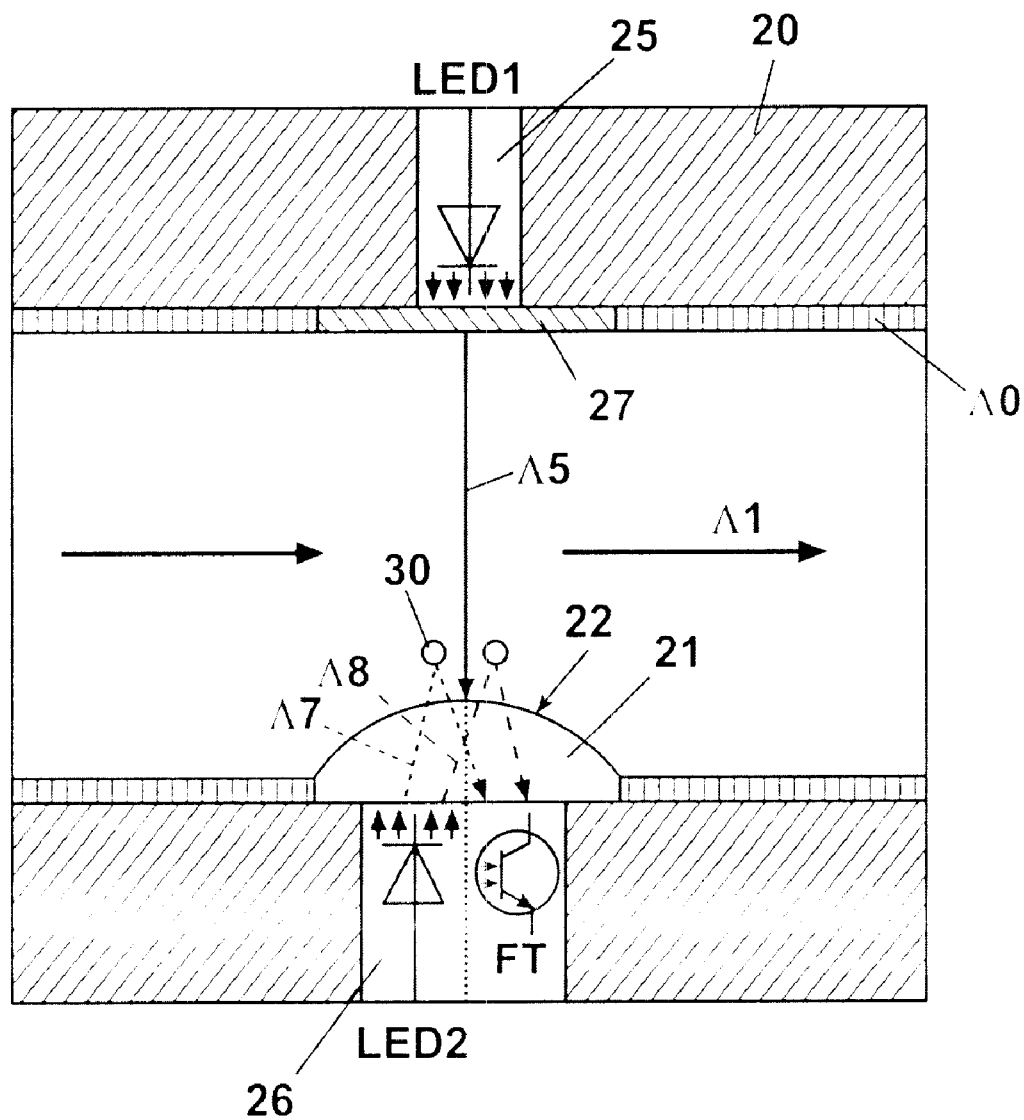
FIG. 3 shows a sectional drawing of a third embodiment example with the known reflection measurement, but with a different type of transparency measurement.

As shown by FIG. 2, the sensor casing 20 can also form, in addition to the sensor body 21, a light guide 24 which deflects the radiation 19 emitted by the additional radiation source LED1 and directs it through the medium 11 on to the boundary surface 22 of the sensor body 21, the reflected portion 16 again being delivered to the single radiation receiver FT or to an additional radiation receiver outside the region of the sensor body 21. In the case of this optical sensor, time multiplex or parallel operation are also possible for detecting the transparency and reflection of the medium 11.

Finally, the additional radiation source LED1 can also be built into the chamber 25 of the channel 10 opposite the sensor body 21 if the radiation 15 is directed transversely relative to the direction of flow of the medium 11. The radiation 15 can pass directly to the single radiation receiver FT, through the sensor body 21. This, however, again requires that the operation of the radiation sources LED1 and LED2 is time-multiplexed. In this case, the chamber 25 must be covered with a light-transmitting cover 27 against the medium 11. The sensor body 21 itself covers the chamber 26 with the radiation source LED2 and the single radiation receiver FT.

We claim:

1. An optical sensor for measuring the property of a gaseous or liquid medium, particularly the opaqueness of a washing or rinsing liquid in a washing or rinsing machine comprising:

a light-transmitting sensor body with an optical boundary surface and an opposite surface, at least one radiation source (LED2) operatively associated with said opposite surface, a radiation receiver (FT) operatively associated with said opposite surface, wherein the sensor body depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index relationships at the boundary surface, and an additional radiation source (LED1) for detecting the transparency of the medium directs a radiation through the medium and the sensor body on to the radiation receiver (FT) such that the radiation receiver (FT) emits, in chronological succession, the measurement signals which are initiated by time-multiplexed operation of radiation sources (LED1, LED2) and which characterise the transparency and reflection of the medium.

2. The optical sensor according to claim 1, wherein the radiation source (LED1) for measuring the transparency of the medium directs the radiation through the medium, transversely relative to the direction of flow of the latter.

3. Optical sensor according to claim 1, wherein light-emitting diodes are used as radiation sources (LED1, LED2) and phototransistors are used as radiation receivers (FT).

4. An optical sensor for measuring the property of a gaseous or liquid medium, particularly the opaqueness of a washing or rinsing liquid in a washing or rinsing machine comprising:

a light-transmitting sensor body with an optical boundary surface and an opposite surface, at least one radiation source (LED2) operatively associated with said opposite surface, a radiation receiver (FT) operatively associated with said opposite surface, wherein the sensor body depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index relationships at the boundary surface, an additional radiation source (LED1) for detecting the transparency of the medium; and an additional radiation receiver (FT), wherein the additional radiation source directs a radiation through the medium on to the additional radiation receiver such that the two radiation receivers (FT) simultaneously emit the measurement signals which are initiated by the assigned radiation sources (LED1, LED2) and which characterise the transparency and reflection of the medium.

5. The optical sensor according to claim 4, wherein the radiation source (LED1) for measuring the transparency of the medium directs the radiation through the medium, transversely relative to the direction of flow of the latter.

6. An optical sensor for measuring the property of a gaseous or liquid medium, particularly the opaqueness of a washing or rinsing liquid in a washing or rinsing machine, with at least one radiation source (LED2), a radiation receiver (FT) and a light-transmitting sensor body, with an optical boundary surface, which, depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index relationships at the boundary surface, comprising:

an additional radiation source (LED1) for detecting the transparency of the medium directs a radiation through the medium and the sensor body on to the radiation receiver (FT) such that the radiation receiver (FT) emits in chronological succession the measurement signals which are initiated by the two time-multiplexed radiation sources (LED1, LED2) and which characterise the transparency and reflection of the medium; and wherein the boundary surface of the light-transmitting sensor body, faces towards the medium and forms a part of a light-transmitting sensor casing which itself forms a part of the channel through which the medium flows, and in that at least the boundary surface of the sensor body projects into the channel.

7. An optical sensor for measuring the property of a gaseous or liquid medium, particularly the opaqueness of a washing or rinsing liquid in a washing or rinsing machine, with at least one radiation source (LED2), a radiation receiver (FT) and a light-transmitting sensor body, with an optical boundary surface, which, depending on the nature of the medium present outside the boundary surface of the sensor body, to a greater or lesser degree transmits to the radiation receiver and/or reflects the radiation directed on to it, resulting at the radiation receiver in different measurement signals which characterise the reflectivity and the refractive index relationships at the boundary surface, comprising:

an additional radiation source (LED1) for detecting the transparency of the medium; and an additional radiation receiver (FT), and the additional radiation source directs a radiation through the medium on to the additional radiation receiver such that the two radiation receivers (FT) simultaneously emit the measurement signals which are initiated by the assigned radiation sources (LED1, LED2) and which characterise the transparency and reflection of the medium;

wherein the radiation source (LED1) for measuring the transparency of the medium directs the radiation through the medium, transversely relative to the direction of flow of the latter, and wherein the boundary surface of the light-transmitting sensor body, faces towards the medium and forms a part of a light-transmitting sensor casing which itself forms a part of the channel through which the medium flows, and in that at least the boundary surface of the sensor body projects into the channel.

8. The optical sensor according to claim 7, wherein the sensor casing accommodates the radiation sources (LED1, LED2) and the radiation receivers (FT), the radiation source (LED2) provided to detect the reflection of the medium and a radiation receiver (FT) being disposed on the sensor body, facing away from the boundary surface of the sensor body, wherein the radiation source (LED1) provided to detect the transparency of the medium and any additional radiation receiver provided for the latter are disposed outside the sensor body, in the sensor casing or in the channel.

9. The optical sensor according to claim 8, wherein the sensor casing comprises in addition to the sensor body a chamber, projecting into the channel and the medium, in which is inserted the radiation source (LED1) provided for detecting the transparency of the medium, which directs its radiation through the medium on to the boundary surface of the sensor body.

10. The optical sensor according to claim 8, wherein the sensor casing forms in addition to the sensor body a light guide, projecting into the medium and the channel, which deflects the radiation emitting from the radiation source (LED1) for detecting the transparency of the medium and directs it through the medium on to the boundary surface of the sensor body.

11. The optical sensor according to claim 8, wherein the radiation source (LED1) provided for detecting the transparency of the medium is disposed on the side of the channel opposite to the sensor body and so that the radiation emitting from this radiation source (LED1) is directed through the sensor body on to a radiation receiver (FT).

12. An optical sensor for measuring the property of a gaseous or liquid medium, particularly the opaqueness of a washing or rinsing liquid in a washing or rinsing machine, comprising:

a light transmitting sensor body;

at least one radiation source (LED2) operatively associated with said sensor body;

at least one radiation receiver (FT) operatively associated with said sensor body;

said sensor body having an optical boundary surface, which, depending on the nature of the medium present outside the boundary-surface of the sensor body, to a greater or lesser degree transmits radiation to the radiation receiver (FT) and/or reflects the radiation directed on to it, resulting at the radiation receiver (FT) in different measurement signals which characterise the reflectivity and the refractive index relationships at the boundary surface; and an additional radiation source (LED1) for detecting the transparency of the medium directs a radiation through the medium and the sensor body on to the radiation receiver (FT) such that the radiation receiver (FT) emits in chronological succession the measurement signals which are initiated by time-multiplexed operation of radiation sources (LED1, LED2) and which characterise the transparency and reflection of the medium.

* * * * *